United States Patent
Farmer et al.

(10) Patent No.: US 11,279,965 B2
(45) Date of Patent: Mar. 22, 2022

(54) **SYMBIOTIC FERMENTATION OF *ACINETOBACTER* AND *BACILLUS* AND APPLICATIONS THEREOF**

(71) Applicant: Locus Oil IP Company, LLC, Solon, OH (US)

(72) Inventors: Sean Farmer, North Miami Beach, FL (US); Ken Alibek, Solon, OH (US); Yajie Chen, Solon, OH (US)

(73) Assignee: LOCUS OIL IP COMPANY, LLC, Solon, OH (US)

( * ) Notice: Subject to any disclaimer, the term of this patent is extended or adjusted under 35 U.S.C. 154(b) by 0 days.

(21) Appl. No.: 16/641,370

(22) PCT Filed: Aug. 27, 2018

(86) PCT No.: PCT/US2018/048122
§ 371 (c)(1),
(2) Date: Feb. 24, 2020

(87) PCT Pub. No.: WO2019/046183
PCT Pub. Date: Mar. 7, 2019

(65) Prior Publication Data
US 2020/0224238 A1 Jul. 16, 2020

Related U.S. Application Data (60) Provisional application No. 62/550,649, filed on Aug. 27, 2017.

(51) Int. Cl.
| | | |
|---|---|---|
| *C12P 39/00* | (2006.01) | |
| *C09K 8/582* | (2006.01) | |
| *C12P 19/04* | (2006.01) | |
| *C12P 21/02* | (2006.01) | |
| *C09K 8/584* | (2006.01) | |
| *C09K 8/588* | (2006.01) | |

(52) U.S. Cl.
CPC ............. *C12P 39/00* (2013.01); *C09K 8/582* (2013.01); *C12P 19/04* (2013.01); *C12P 21/02* (2013.01); *C09K 8/584* (2013.01); *C09K 8/588* (2013.01)

(58) Field of Classification Search
CPC ........... C12P 21/02; C12P 19/04; C12P 39/00; C12P 7/6436; C09K 8/582; C09K 8/584; C09K 8/588
See application file for complete search history.

(56) References Cited

U.S. PATENT DOCUMENTS

| | | |
|---|---|---|
| 4,450,908 A | 5/1984 | Hitzman |
| 5,165,477 A | 11/1992 | Shell et al. |
| 5,821,112 A * | 10/1998 | Botto et al. .................. 435/262 |
| 9,422,470 B2 | 8/2016 | Xu et al. |
| 9,725,986 B2 | 8/2017 | Xu et al. |
| 2002/0143071 A1 | 10/2002 | Gutnick et al. |
| 2003/0008377 A1 * | 1/2003 | Lee et al. .................. 435/252.1 |
| 2010/0044031 A1 | 2/2010 | Fallon et al. |
| 2013/0062053 A1 | 3/2013 | Kohr et al. |
| 2014/0315765 A1 | 10/2014 | McDaniel |
| 2015/0037302 A1 | 2/2015 | Bralkowski et al. |
| 2016/0222280 A1 | 8/2016 | Kohr et al. |

FOREIGN PATENT DOCUMENTS

| | | |
|---|---|---|
| CN | 102352227 A | 2/2012 |
| WO | 2014152350 A1 | 9/2014 |
| WO | 2017044953 A1 | 3/2017 |

OTHER PUBLICATIONS

Amani, H., et al., "Comparative study of biosurfactant producing bacteria in MEOR applications." Journal of Petroleum Science and Engineering. 2010, 75: 209-214.

Bach, H., et al., "An Exocellular Protein from the Oil-Degrading Microbe Acinetobacter venetianus RAG-1 Enhances the Emulsifying Activity of the Polymeric Bioemulsifier Emulsan." Applied and Environmental Microbiology, May 2003, 69(5): 2608-2615.

Ghojavand, H. et al., "Isolation of thermotolerant, halotolerant, facultative biosurfactant-producing bacteria." Appl. Microbiol. Biotechnol, Oct. 2008, 80(6): Abstract, doi: 10,1007/s00253-008-1570-7.

Sharma, A. et al., "A study on biosurfactant production in Lactobacillus and *Bacillus* sp." Int. J. Curr. Microbiol. App. Sci., 2014, 3(11): 723-733.

* cited by examiner

*Primary Examiner* — Satyendra K Singh
(74) *Attorney, Agent, or Firm* — Saliwanchik, Lloyd & Eisenschenk (57) ABSTRACT

The subject invention provides microbe-based products and efficient methods of producing them. In specific embodiments, methods are provided for symbiotic cultivation of *Acinetobacter venetianus* RAG1 and *Bacillus subtilis* B1, as well as growth by-products thereof. Methods are also provided for using the subject microbe-based products, for example, in microbially enhanced oil recovery (MEOR).

3 Claims, 2 Drawing Sheets

|  | Surfactin concentration (g/L) | Peak height of Emulsan |
|---|---|---|
| RAG1 B1 Glucose | 0.3 | 5413 |
| RAG1 B1 Glycerol | 0 | 976 |
| RAG1 Glucose | 0 | 1303 |
| RAG1 Glycerol | 0 | 1280 |
| RAG1 Isopropyl alcohol | 0 | 1280 |
| RAG1 Ethanol | 0 | 1297 |

FIG. 3

SYMBIOTIC FERMENTATION OF *ACINETOBACTER* AND *BACILLUS* AND APPLICATIONS THEREOF

This application is a National Stage Application of International Application No. PCT/US2018/048122, filed Aug. 27, 2018; which claims the priority benefit of U.S. provisional application Ser. No. 62/550,649, filed Aug. 27, 2017, both of which are incorporated herein by reference in their entirety.

BACKGROUND OF THE INVENTION

Cultivation of microorganisms such as bacteria, yeast and fungi is important for the production of a wide variety of useful bio-preparations. Microorganisms play crucial roles in, for example, food industries, pharmaceuticals, agriculture, oil and gas recovery, mining, environmental remediation, and waste management; however, one of the factors restricting commercialization of microbe-based products has been the cost per propagule density, as it is particularly expensive and unfeasible to apply microbial products to large scale operations with sufficient inoculum to see the benefits.

Two principle forms of microbe cultivation exist: submerged cultivation and surface cultivation. Bacteria, yeasts and fungi can all be grown using either the surface or submerged cultivation methods. Both cultivation methods require a nutrient medium for the growth of the microorganisms. The nutrient medium, which can either be in a liquid or a solid form, typically includes a carbon source, a nitrogen source, salts and appropriate additional nutrients and microelements. The pH and oxygen levels are maintained at values suitable for a given microorganism.

Microbes have great potential to be beneficial to a wide variety of industries. One area in particular where microbes have already provided promising benefits is the oil and gas industry through microbially enhanced oil recovery (MEOR). As oil wells mature, it becomes more difficult and costly to continue to pump oil at an economically viable rate. Oil wells that are nearing the end of their economically useful life are called "marginal" or "stripper" wells. These wells often go abandoned prematurely, leaving behind hundreds or even thousands of barrels of valuable and useful crude oil. Therefore, there is a continuing need to develop improved methods of oil recovery, even from wells that might be considered too mature to be productive.

Oil exists in small pores and narrow fissures within the body of reservoir rocks underneath the surface of the earth. Natural pressure of the reservoir causes the oil to flow up to the surface, thereby providing primary production; however as oil production progresses, the reservoir pressure is depleted to a point at which artificial lift or pumping is required to maintain an economical oil production rate.

When it is necessary to provide external energy for the reservoir to achieve additional oil recovery (secondary recovery, or enhanced oil recovery (EOR)), the extra energy can be introduced by injecting gas (gas injection) and/or water (water flooding). With water flooding in particular, water is injected into the subterranean oil reservoir for the purpose of displacing the crude oil from the pore spaces of the reservoir rock towards the producing wells.

Primary recovery generally results in an average recovery of only a fraction of the oil originally present in an oil bearing formation. Secondary recovery generally recovers another 10% by the time it becomes uneconomical to continue. It is not unusual, then, for 60 to 70% of the oil originally in the formation to remain, even after secondary recovery reaches is economical limit. In this situation, a third stage of oil recovery/EOR, so-called tertiary production, can be considered.

At this tertiary stage, technically advanced methods are employed to either modify the properties of reservoir fluids or the reservoir rock characteristics. In general, the methods can be classified into four main categories as thermal methods, chemical methods, miscible or solvent injection, and microbial methods.

Microbial enhanced oil recovery (MEOR) in particular is a multidisciplinary field incorporating, among others: geology, chemistry, microbiology, fluid mechanics, petroleum engineering, environmental engineering and chemical engineering. The microbial processes proceeding in MEOR can be classified according to the oil production problem in the field: well bore clean-up removes mud and other debris blocking the channels where oil flows; well stimulation improves the flow of oil from the drainage area into the well bore; and enhanced water floods increase microbial activity by injecting selected microbes and sometimes nutrients.

Thus, MEOR uses microorganisms and/or their metabolites to enhance the recovery of residual oil. Nutrients and suitable bacteria, which preferably grow under the anaerobic reservoir conditions, are injected into the reservoir. Microbial by-products, which can include biosurfactants, biopolymers, acids, solvents, gases, and enzymes, for example, can modify the properties of the oil and the interactions between oil, water, and the porous media, alter the permeability of subterranean formations, and ultimately increase the mobility and recovery of oil.

Specifically, interest in microbial surfactants has been steadily increasing in recent years due to their diversity, environmentally friendly nature, possibility of large-scale production, selectivity, performance under extreme conditions, and potential applications in environmental protection. Microbially-produced surfactants, i.e., biosurfactants reduce the interfacial tension between water and oil and, therefore, a lower hydrostatic pressure is required to move the liquid entrapped in the pores to overcome the capillary effect. Secondly, biosurfactants contribute to the formation of micelles providing a physical mechanism to mobilize oil in a moving aqueous phase.

Other microbial by-products have also increased in importance, including certain enzymes, acids, gases and biopolymers; however, there is still a need for methods of large scale cultivation of these products, and in particular the microbes that produce them, in viable forms. For example, many microbes are difficult to grow and subsequently deploy to oil production operations in sufficient quantities to be useful. This problem is exacerbated by losses in viability and/or activity due to processing, formulating, storage, and stabilizing prior to distribution.

Furthermore, once applied, biological products may not thrive for any number of reasons including, for example, insufficient initial cell densities, the inability to compete effectively with the existing microflora at a particular location, and being introduced to formations and/or other environmental conditions in which the microbe cannot flourish or even survive.

Microbe-based compositions could help resolve some of the aforementioned issues faced by the oil and gas industry, if only they could be made more readily available and, preferably, in a more active form. Thus, there is a need for more efficient cultivation methods for mass production of microorganisms and microbial metabolites.

BRIEF SUMMARY OF THE INVENTION

The subject invention provides microbes, as well as by-products of their growth, such as biosurfactants and/or other metabolites. The subject invention also provides methods of using and producing these microbes and their by-products. Advantageously, the microbe-based products and methods of the subject invention are environmentally-friendly, operational-friendly and cost-effective.

In certain embodiments, the subject invention provides materials and methods for producing microbe-based products at any scale desired, from small (e.g., laboratory) scale to large (e.g., industrial) scale. In particular, methods are provided for symbiotic cultivation of an *Acinetobacter* spp. bacterium and a *Bacillus* spp. bacterium, as well as products of the growth of those microbes. Advantageously, total cell biomass produced by the subject methods is greater than when pure cultures of the individual microbes are cultivated on their own.

In certain preferred embodiments, methods for cultivating microorganisms are provided, the methods comprising inoculating a fermentation system with a first microorganism and a second microorganism, wherein the first microorganism is a strain of *Acinetobacter venetianus* and the second microorganism is a strain of *Bacillus subtilis*. Even more preferably, in one embodiment, the strain of *A. venetianus* is "RAG1" and the strain of *B. subtilis* is "B1."

In one embodiment of the subject methods, the system is provided with a carbon source. Preferably, the carbon source is glucose. The microorganisms can then be incubated for a time period sufficient to achieve a desired effect, e.g., production of a desired amount of cell biomass or a desired amount of one or more microbial growth by-products.

In one embodiment, the subject invention provides methods of producing one or more desirable growth by-products of a microorganism by cultivating a microbe strain of the subject invention under conditions appropriate for growth and production of the desired one or more growth by-products; and optionally, purifying the by-products. In certain embodiments, cultivation of the microbe strain is performed according to the symbiotic cultivation methods of the subject invention. Examples of growth by-products according to the subject invention include biosurfactants, biopolymers, enzymes, acids, proteins, amino acids, and others.

Figure 3:
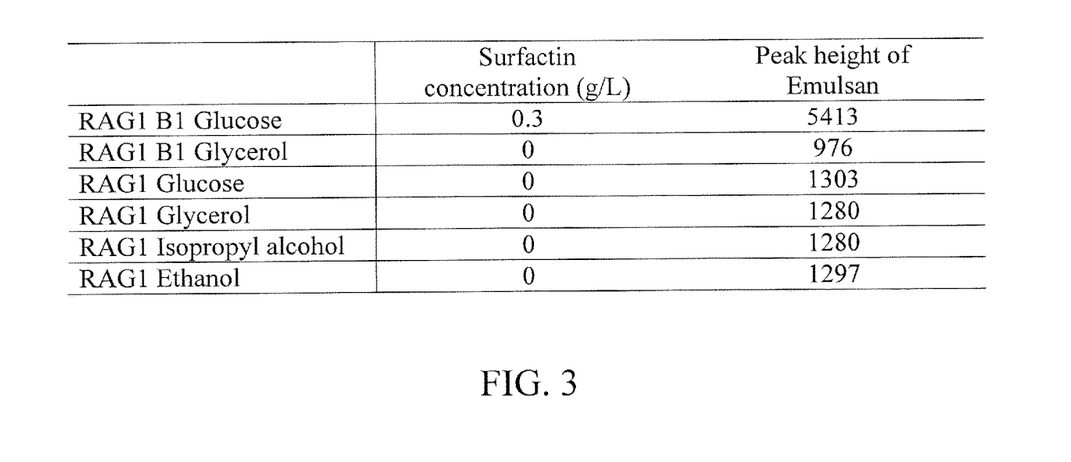
FIG. 3 shows biosurfactant production of RAG1 and B1 in various systems. Both emulsan and surfactin production were highest in RAG1 B1 glucose systems.

In specific embodiments, the growth by-products are one or more biosurfactants, such as, e.g., surfactin, and/or one or more biopolymers, such as e.g., emulsan. Advantageously, as shown in FIG. 3, the methods of the subject invention produce greater biosurfactant and/or biopolymer concentrations than when pure cultures of the individual microbes are cultivated on their own.

In certain embodiments, the subject invention provides materials and methods for increasing oil production by treating an oil well and/or oil recovery equipment with microorganisms produced according to the subject methods and/or their growth by-products. In additional embodiments, the microorganisms and/or their by-products can be used in remediation processes for cleaning up an oil spill.

In certain embodiments, the microbe-based products produced by the subject methods, can be used in, for example, improved oil production, bioremediation and mining; waste disposal and treatment; promoting plant health and productivity; and reclaiming and/or restoring the health of soils.

DETAILED DESCRIPTION

In certain embodiments, the subject invention provides materials and methods for producing microbe-based products at any scale desired, from small (e.g., laboratory) scale to large (e.g., industrial) scale. In particular, methods are provided for symbiotic cultivation of an *Acinetobacter* spp. bacterium and a *Bacillus* spp. bacterium, as well as products of the growth of those microbes. Advantageously, total cell biomass produced by the subject methods is greater than when pure cultures of the individual microbes are cultivated on their own.

In certain preferred embodiments, methods for cultivating microorganisms are provided, the methods comprising inoculating a fermentation system with a first microorganism and a second microorganism, wherein the first microorganism is a strain of *Acinetobacter venetianus* and the second microorganism is a strain of *Bacillus subtilis*. Even more preferably, in one embodiment, the strain of *A. venetianus* is "RAG1" and the strain of *B. subtilis* is "B1."

In one embodiment of the subject methods, the system is provided with a carbon source. Preferably, the carbon source is glucose.

In one embodiment, the subject invention provides methods of producing one or more desirable growth by-products of a microorganism by cultivating a microbe strain of the subject invention under conditions appropriate for growth and production of the desired one or more growth by-products; and optionally, purifying the by-products. In certain embodiments, cultivation of the microbe strain is performed according to the symbiotic cultivation methods of the subject invention.

In specific embodiments, the growth by-products are one or more biosurfactants, such as, e.g., surfactin, and/or one or more biopolymers, such as e.g., emulsan. Advantageously, as shown in FIG. 3, the methods of the subject invention produce greater biosurfactant and/or biopolymer concentrations than when pure cultures of the individual microbes are cultivated on their own.

Selected Definitions

As used herein, reference to a "microbe-based composition" means a composition that comprises components that were produced as the result of the growth of microorganisms or other cell cultures. Thus, the microbe-based composition may comprise the microbes themselves and/or by-products of microbial growth. The microbes may be in a vegetative state or in spore form, or a mixture of both. The microbes may be planktonic or in a biofilm form, or a mixture of both. The by-products of growth may be, for example, metabolites (e.g., biosurfactants), cell membrane components, expressed proteins, and/or other cellular components. The microbes may be intact or lysed. The cells or spores may be totally absent, or present at, for example, a concentration of $1 \times 10^4$, $1 \times 10^5$, $1 \times 10^6$, $1 \times 10^7$, $1 \times 10^8$, $1 \times 10^9$, $1 \times 10^{10}$, or $1 \times 10^{11}$ or more cells or spores per milliliter of the composition.

The subject invention further provides "microbe-based products," which are products that are to be applied in practice to achieve a desired result. The microbe-based product can be simply the microbe-based composition harvested from the microbe cultivation process. Alternatively, the microbe-based product may comprise further ingredients that have been added. These additional ingredients can include, for example, stabilizers, buffers, carriers (e.g., water or salt solutions), added nutrients to support further microbial growth, non-nutrient growth enhancers and/or agents that facilitate tracking of the microbes and/or the composition in the environment to which it is applied. The microbe-based product may also comprise mixtures of microbe-based compositions. The microbe-based product may also comprise one or more components of a microbe-based composition that have been processed in some way such as, but not limited to, filtering, centrifugation, lysing, drying, purification and the like.

A "metabolite" refers to any substance produced by metabolism (e.g., a growth by-product) or a substance necessary for taking part in a particular metabolic process. A metabolite can be an organic compound that is a starting material (e.g., glucose), an intermediate (e.g., acetyl-CoA) in, or an end product (e.g., n-butanol) of metabolism. Examples of metabolites include, but are not limited to, enzymes, acids, solvents, gasses, alcohols, proteins, vitamins, minerals, microelements, amino acids, polymers, and surfactants.

As used herein, an "isolated" or "purified" nucleic acid molecule, polynucleotide, polypeptide, protein, organic compound such as a small molecule (e.g., those described below), or other compound is substantially free of other compounds, such as cellular material, with which it is associated in nature. For example, a purified or isolated polynucleotide (ribonucleic acid (RNA) or deoxyribonucleic acid (DNA)) is free of the genes or sequences that flank it in its naturally-occurring state. A purified or isolated polypeptide is free of the amino acids or sequences that flank it in its naturally-occurring state. A purified or isolated microbial strain is removed from the environment in which it exists in nature. Thus, the isolated strain may exist as, for example, a biologically pure culture, or as spores (or other forms of the strain) in association with a carrier.

In certain embodiments, purified compounds are at least 60% by weight (dry weight) the compound of interest. Preferably, the preparation is at least 75%, more preferably at least 90%, and most preferably at least 99%, by weight the compound of interest. For example, a purified compound is one that is at least 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis.

As used herein, "polymer" refers to any macromolecular compound prepared by bonding one or more similar molecular units, called monomers, together. Polymers include synthetic and natural polymers. Exemplary polymers include rubbers, starches, resins, gums (e.g., guar gum, xanthan gum, and welan gum), neoprene, nylon, PVC, silicone, cellulose, polystyrene, polyethylene, polypropylene, polyacrylonitrile, polyamines, polysaccharides (e.g., emulsan), polynucleotides, polybutylene adipate terephthalate (PBAT), polyhydroxyalkanoates (PHAs), polybytlene succinate (PBS), polycaprolactone (PCL), polyglycolic acid (PGA), polyhydroxybutyrates (PHBs), polyesters such as polylactide (PLA), polyacrylamides (PAM), and others.

Further included in the term polymer is the term "biopolymer," "biological polymer" or "renewable polymer," which as used herein, means a natural polymeric substance, or a polymeric substance occurring in a living organism. One characteristic of biopolymers is their ability to biodegrade. Biopolymers can include polynucleotides (e.g., RNA and DNA), polysaccharides (e.g., linearly bonded polymeric carbohydrates), and polypeptides (i.e., short polymers of amino acids). Specific examples of biopolymers include, but are not limited to, rubbers, emulsan, suberin, melanin, lignin, cellulose, xanthan gum, guar gum, welan gum, levan, alginate, and many others.

As used herein, "reduces" means a negative alteration of at least 1%, 5%, 10%, 25%, 50%, 75%, or 100%.

As used herein, "reference" means a standard or control condition.

As used herein, "salt-tolerant" in the context of a microbe means the microbe is capable of growing in a sodium chloride concentration of 15% or greater. In a specific embodiment, "salt-tolerant" refers to the ability to grow in 150 g/L or more of NaCl.

As used herein, "surfactant" means a compound that lowers the surface tension (or interfacial tension) between two liquids or between a liquid and a solid. Surfactants act as, e.g., detergents, wetting agents, emulsifiers, foaming agents, and/or dispersants. A "biosurfactant" is a surface-active substance produced by a living cell.

As used herein, "symbiotic fermentation" means co-cultivation of more than one microorganism in a single fermentation system. Typically, the more than one microorganisms, which can be a mixture of various types of yeasts, bacteria, fungi, and others, interact symbiotically to produce a desired effect, e.g., a desired amount of cell biomass growth or a desired amount of metabolite production. In one embodiment, this symbiotic relationship can result in a synergistically enhanced effect, for example, the desired effect can be magnified when compared to what results from cultivating only one of the chosen microorganisms on its own.

The transitional term "comprising," which is synonymous with "including," or "containing," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Unless specifically stated or obvious from context, as used herein, the term "or" is understood to be inclusive. Unless specifically stated or obvious from context, as used herein, the terms "a," "and," and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

Other features and advantages of the invention will be apparent from the following description of the preferred embodiments thereof, and from the claims. All references cited herein are hereby incorporated by reference.

Growth of Microbes According to the Subject Invention

The subject invention provides methods for co-cultivation of microorganisms and production of microbial metabolites and/or other by-products of microbial growth. The microbial cultivation systems would typically use submerged culture fermentation; however, surface culture and modified or hybrid systems can also be used. As used herein "fermentation" refers to cultivation or growth of cells under controlled conditions. The growth could be aerobic or anaerobic.

In preferred embodiments, the methods comprise inoculating a fermentation system with a first microorganism and a second microorganism. In certain embodiments, the first microorganism can be a bacterium from the genus *Acinetobacter* and the second microorganism can be a bacterium from the genus *Bacillus*.

In a specific embodiment, the first microorganism is a strain of *Acinetobacter venetianus*, preferably "RAG1," and the second microorganism is a strain of *Bacillus subtilis*, preferably "B1."

In one embodiment, the method further comprises adding a carbon source to the fermentation system. In preferred embodiments, the carbon source is glucose. Typically, *Acinetobacter* prefer ethanol as a carbon source, and do not thrive when glucose is used as a carbon source. Surprisingly, however, when grown according to the subject methods, *Acinetobacter* exhibits increased growth and metabolite production despite the use of glucose.

The method then comprises incubating the first and second microorganisms in the fermentation system until a desired result is achieved, for example, a desired amount of cell biomass or a desired amount of one or more microbial metabolites has been produced.

In one embodiment, the microbe-based products are obtained through cultivation processes ranging from small to large scales. These cultivation processes include, but are not limited to, submerged cultivation/fermentation, solid state fermentation (SSF), and hybrids, modifications and combinations thereof.

In one embodiment, the subject invention provides materials and methods for the production of biomass (e.g., viable cellular material), extracellular metabolites (e.g. small molecules and excreted proteins), residual nutrients and/or intracellular components (e.g. enzymes and other proteins).

In one embodiment, the subject invention provides methods of producing a microbial metabolite or growth by-product, such as, e.g., a biosurfactant or a biopolymer, by cultivating a microbe strain of the subject invention under conditions appropriate for growth and production of the metabolite or growth by-product.

The microbial growth by-product produced by microorganisms of interest may be retained in the microorganisms or secreted into the growth medium. In another embodiment, the method for producing microbial growth by-products may further comprise steps of concentrating and purifying the microbial growth by-product of interest. Alternatively, the microbial growth by-products can be utilized in their crude form, meaning no purification is performed. In a further embodiment, the growth medium may contain compounds that stabilize the activity of the microbial growth by-product.

The microbe growth vessel used according to the subject invention can be any fermenter or cultivation reactor for industrial use. In one embodiment, the vessel may have functional controls/sensors or may be connected to functional controls/sensors to measure important factors in the cultivation process, such as pH, oxygen, pressure, temperature, agitator shaft power, humidity, viscosity and/or microbial density and/or metabolite concentration.

In a further embodiment, the vessel may also be able to monitor the growth of microorganisms inside the vessel (e.g., measurement of cell number and growth phases). Alternatively, a daily sample may be taken from the vessel and subjected to enumeration by techniques known in the art, such as dilution plating technique. Dilution plating is a simple technique used to estimate the number of microbes in a sample. The technique can also provide an index by which different environments or treatments can be compared.

In one embodiment, the method includes supplementing the cultivation with a nitrogen source. The nitrogen source can be, for example, potassium nitrate, ammonium nitrate, ammonium sulfate, ammonium phosphate, ammonia, urea, and/or ammonium chloride. These nitrogen sources may be used independently or in a combination of two or more.

The method can provide oxygenation to the growing culture. One embodiment utilizes slow motion of air to remove low-oxygen containing air and introduce oxygenated air. The oxygenated air may be ambient air supplemented daily through mechanisms including impellers for mechanical agitation of the liquid, and air spargers for supplying bubbles of gas to the liquid for dissolution of oxygen into the liquid.

The method can further comprise supplementing the cultivation with a carbon source. The carbon source is typically a carbohydrate, such as glucose, sucrose, lactose, fructose, trehalose, mannose, mannitol, and/or maltose; organic acids such as acetic acid, fumaric acid, citric acid, propionic acid, malic acid, malonic acid, and/or pyruvic acid; alcohols such as ethanol, propanol, butanol, pentanol, hexanol, isobutanol, and/or glycerol; fats and oils such as soybean oil, rice bran oil, olive oil, corn oil, sesame oil, and/or linseed oil; etc.

These carbon sources may be used independently or in a combination of two or more, although in preferred embodiments, the carbon source comprises glucose.

In one embodiment, growth factors and trace nutrients for microorganisms are included in the medium. This is particularly preferred when growing microbes that are incapable of producing all of the vitamins they require. Inorganic nutrients, including trace elements such as iron, zinc, copper, manganese, molybdenum and/or cobalt may also be included in the medium. Furthermore, sources of vitamins, essential amino acids, and microelements can be included, for example, in the form of flours or meals, such as corn flour, or in the form of extracts, such as yeast extract, potato extract, beef extract, soybean extract, banana peel extract, and the like, or in purified forms. Amino acids such as, for example, those useful for biosynthesis of proteins, can also be included.

In one embodiment, inorganic salts may also be included. Usable inorganic salts can be potassium dihydrogen phosphate, dipotassium hydrogen phosphate, disodium hydrogen phosphate, magnesium sulfate, magnesium chloride, iron sulfate, iron chloride, manganese sulfate, manganese chloride, zinc sulfate, lead chloride, copper sulfate, calcium chloride, calcium carbonate, and/or sodium carbonate. These inorganic salts may be used independently or in a combination of two or more.

In some embodiments, the method for cultivation may further comprise adding additional acids and/or antimicrobials in the liquid medium before and/or during the cultivation process. Antimicrobial agents or antibiotics are used for protecting the culture against contamination. Additionally, antifoaming agents may also be added to prevent the formation and/or accumulation of foam when gas is produced during cultivation.

The pH of the mixture should be suitable for the microorganism of interest. Buffers, and pH regulators, such as carbonates and phosphates, may be used to stabilize pH near a preferred value. When metal ions are present in high concentrations, use of a chelating agent in the liquid medium may be necessary.

The method and equipment for cultivation of microorganisms and production of the microbial by-products can be performed in a batch, quasi-continuous, or continuous processes.

In one embodiment, the method for cultivation of microorganisms is carried out at about 5° to about 100° C., preferably, 15 to 60° C., more preferably, 25 to 45° C. In a further embodiment, the cultivation may be carried out continuously at a constant temperature. In another embodiment, the cultivation may be subject to changing temperatures.

In one embodiment, the equipment used in the method and cultivation process is sterile. The cultivation equipment such as the reactor/vessel may be separated from, but connected to, a sterilizing unit, e.g., an autoclave. The cultivation equipment may also have a sterilizing unit that sterilizes in situ before starting the inoculation. Air can be sterilized by methods know in the art. For example, the ambient air can pass through at least one filter before being introduced into the vessel. In other embodiments, the medium may be pasteurized or, optionally, no heat at all added, where the use of low water activity and low pH may be exploited to control bacterial growth.

In one embodiment, the subject invention further provides a method for producing other microbial metabolites such as enzymes, ethanol, lactic acid, beta-glucan, proteins, peptides, metabolic intermediates, polyunsaturated fatty acid, and lipids. The metabolite content produced by the method can be, for example, at least 20%, 30%, 40%, 50%, 60%, 70%, 80%, or 90%.

The biomass content of the fermentation broth may be, for example from 5 g/l to 180 g/l or more. In one embodiment, the solids content of the broth is from 10 g/l to 150 g/l.

In one embodiment, all of the microbial cultivation composition is removed upon the completion of the cultivation (e.g., upon, for example, achieving a desired cell density, or density of a specified metabolite in the broth). In this batch procedure, an entirely new batch is initiated upon harvesting of the first batch.

In another embodiment, only a portion of the fermentation product is removed at any one time. In this embodiment, biomass with viable cells remains in the vessel as an inoculant for a new cultivation batch. The composition that is removed can be a cell-free broth or contain cells.

In this manner, a quasi-continuous system is created.

Advantageously, the method does not require complicated equipment or high energy consumption. The microorganisms of interest can be cultivated at small or large scale on site and utilized, even being still-mixed with their media. Similarly, the microbial metabolites can also be produced at large quantities at the site of need.

Advantageously, the microbe-based products can be produced in remote locations. The microbe growth facilities may operate off the grid by utilizing, for example, solar, wind and/or hydroelectric power.

Microbial Strains Grown in Accordance with the Subject Invention

The microorganisms grown according to the systems and methods of the subject invention can be, for example, bacteria, yeast and/or fungi. These microorganisms may be natural, or genetically modified microorganisms. For example, the microorganisms may be transformed with specific genes to exhibit specific characteristics. The microorganisms may also be mutants of a desired strain. As used herein, "mutant" means a strain, genetic variant or subtype of a reference microorganism, wherein the mutant has one or more genetic variations (e.g., a point mutation, missense mutation, nonsense mutation, deletion, duplication, frameshift mutation or repeat expansion) as compared to the reference microorganism. Procedures for making mutants are well known in the microbiological art. For example, UV mutagenesis and nitrosoguanidine are used extensively toward this end.

In preferred embodiments, the microorganisms are bacteria, including Gram-positive and Gram-negative bacteria. The bacteria may be, for example *Acinetobacter* (e.g., *A. calcoaceticus, A. baumannii, A. venetianus*), *Agrobacterium* (e.g., *A. radiobacter*), *Azobacter* (e.g., *A. vinelandii, A. chroococcum*), *Azospirillum* (e.g., *A. brasiliensis*), *Bacillus* (e.g., *B. subtilis, B. licheniformis, B. firmus, B. laterosporus, B. megaterium, B. amyloliquefaciens*), *Clostridium* spp. (*C. butyricum, C. tyrobutyricum, C. acetobutyricum,* and *C. beijerinckii*), *Pseudomonas* (e.g., *P. chlororaphis* subsp. *aureofaciens* (Kluyver)), *Ralslonia* (e.g., *R. eulropha*), *Rhizobium, Rhodospirillum* (e.g., *R. rubrum*), and/or *Sphingomonas paucimobilis*.

In specific embodiments, the first microorganism is selected from strains of *Acinetobacter*. Members of this Gram-negative, aerobic, non-fermenting genus can be isolated from a broad range of different habitats, including water, soil and living organisms and, despite having been described as non-motile, possess different forms of motility (e.g., twitching).

Preferably, the strain is *Acinetobacter venetianus* RAG1 (ATCC 31012). *A. venetianus* strains are a useful tool in oil recovery and bioremediation, as they have developed diverse strategies of degrading n-alkanes, such as those found in crude oil. RAG1, in particular, can produce, for example, emulsan and esterases for such a purpose.

In one embodiment, the second microorganism is a strain of *Bacillus*. Preferably, the strain is a strain of *B. subtilis*, such as, for example, *B. subtilis* var. *locuses* B1 or B2, which are effective producers of, for example, surfactin and other biosurfactants, as well as biopolymers. In this regard, WO 2017/044953 is incorporated herein, in its entirety, by reference.

In certain embodiments, the present invention utilizes *Bacillus subtilis* strains with enhanced biosurfactant production compared to wild type *Bacillus subtilis* as well as compared to other microbes used in oil recovery. Such *Bacillus subtilis* have been termed members of the B series, including, but not limited to, B1, B2 and B3.

*Bacillus subtilis* strain B1 is a facultative aerobe growing in a temperature range of 25–55° C., with optimal growth temperature at 35° C. The vegetative cells of B1 are rods that are 0.7 to 0.9 μm wide by 1.6 to 3.3 μm long and occur singly. It is motile, Gram positive and produces biopolymers on nutrient agar and potato dextrose agar. It hydrolyzes starch, is positive on Voges-Proskauer test and can utilize citrate. Furthermore, B1 produces ellipsoidal spores centrally or paracentrally in unswollen sporangia. The size of mature spores is 0.8 to 1.0 μm wide by 1.6 to 1.9 μm long.

In certain embodiments, the *Bacillus subtilis* strains are salt tolerant. In a specific embodiment, salt tolerant refers to the ability to grow in 150 g/L, or 15%, or more of NaCl.

In certain embodiments, the *Bacillus subtilis* strains are capable of thriving under low oxygen conditions. The strains are also capable of growing under anaerobic conditions.

In certain embodiments, such strains are characterized by enhanced biosurfactant production compared to wild type *Bacillus subtilis* strains. The B strain series of *Bacillus subtilis* produce more biosurfactant compared to reference strains of *Bacillus subtilis*.

In certain embodiments, the *Bacillus subtilis* strains have increased biopolymer solvent and/or enzyme production. The *Bacillus subtilis* B series strains can also be used for producing enzymes that degrade or metabolize oil or other petroleum products.

Figure 1:
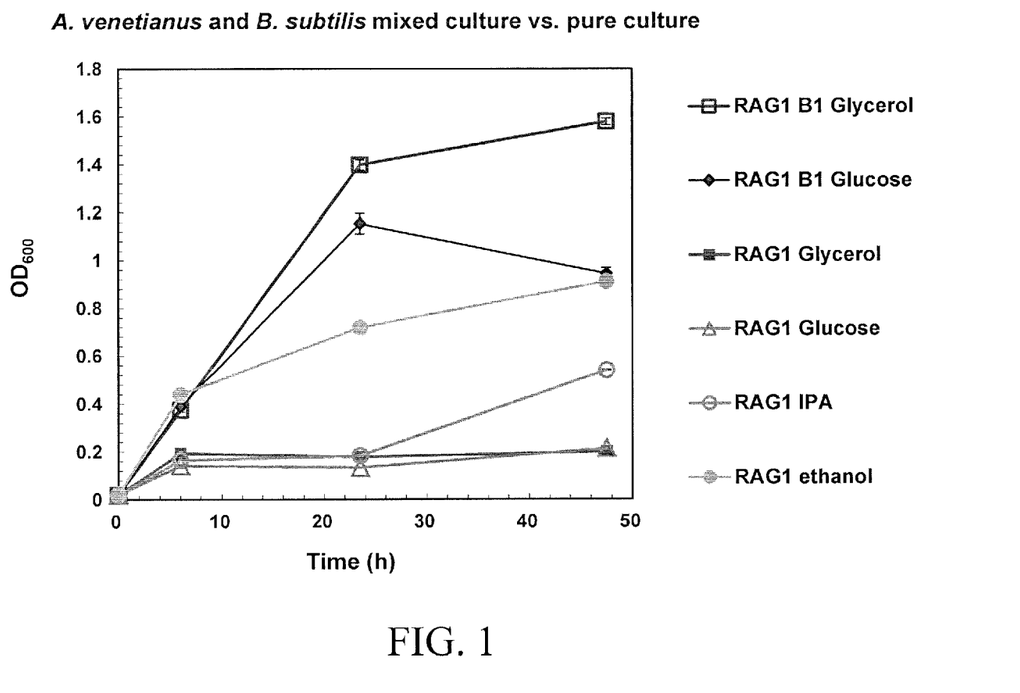
FIG. 1 shows optical density at 600 nm in different systems (mixed culture of *A. venetianus* RAG1 and *B. subtilis* B1, or pure culture of *A. venetianus* RAG1) using four different carbon sources for representation of cell biomass growth.

In preferred embodiments, RAG1 and B1 are co-cultivated, i.e. through symbiotic fermentation. Advantageously, as shown in FIG. 1 the cell biomass from symbiotic growth of these two strains is greater than when pure cultures of the individual microbes are cultivated. Furthermore, as shown in FIG. 3 production of biosurfactants and/or biopolymers in symbiotic culture is greater than when pure cultures of the individual microbes are used.

Microbial Growth By-Products

The methods and systems of the subject invention can be used to produce compositions comprising useful microbial growth by-products such as, for example, biosurfactants, biopolymers and/or other microbial metabolites.

In specific embodiments, the growth by-product is a lipopeptide biosurfactant selected from surfactin, iturin, lichenysin and fengycin. In other specific embodiments, the growth by-product is a biopolymer, such as, for example, emulsan.

In a specific embodiment, the growth by-products produced according to the subject invention are surfactin and emulsan.

Due to the structure and composition of biosurfactants, they possess excellent surface and interfacial tension reduction properties, as well as other beneficial biochemical properties, which can be useful in applications such as large scale oil and gas, industrial and agriculture uses, and in other fields, including but not limited to cosmetics, household products, and health, medical and pharmaceutical fields.

Biosurfactants are a structurally diverse group of surface-active substances produced by microorganisms. Biosurfactants are biodegradable and can be easily and cheaply produced using selected organisms on renewable substrates. Most biosurfactant-producing organisms produce biosurfactants in response to the presence of a hydrocarbon source (e.g., oils, sugar, glycerol, etc.) in the growing media. Other media components, such as concentration of iron, can also affect biosurfactant production significantly.

All biosurfactants are amphiphiles. They consist of two parts: a polar (hydrophilic) moiety and non-polar (hydrophobic) group. Due to their amphiphilic structure, biosurfactants increase the surface area of hydrophobic water-insoluble substances, increase the water bioavailability of such substances, and change the properties of bacterial cell surfaces.

Biosurfactants include low molecular weight glycolipids (e.g., rhamnolipids, sophorolipids, mannosylerythritol lipids), lipopeptides (e.g., surfactin), flavolipids, phospholipids, and high molecular weight polymers (e.g., emulsan), such as lipoproteins, lipopolysaccharide-protein complexes, and polysaccharide-protein-fatty acid complexes. The common lipophilic moiety of a biosurfactant molecule is the hydrocarbon chain of a fatty acid, whereas the hydrophilic part is formed by ester or alcohol groups of neutral lipids, by the carboxylate group of fatty acids or amino acids (or peptides), organic acid in the case of flavolipids, or, in the case of glycolipids, by the carbohydrate.

Biosurfactants accumulate at interfaces, thus reducing interfacial tension and leading to the formation of aggregated micellular structures in solution. Safe, effective microbial biosurfactants reduce the surface and interfacial tensions between the molecules of liquids, solids, and gases. The ability of biosurfactants to form pores and destabilize biological membranes permits their use as antibacterial, antifungal, and hemolytic agents.

Combined with the characteristics of low toxicity and biodegradability, biosurfactants are advantageous for use in the oil and gas industry for a wide variety of petroleum industry applications, such as microbially enhanced oil recovery. These applications include, but are not limited to, enhancement of crude oil recovery from an oil-containing formation; stimulation of oil and gas wells (to improve the flow of oil into the well bore); removal of contaminants and/or obstructions such as biofilms, paraffins, asphaltenes and scale from equipment such as rods, tubing, liners, tanks and pumps; prevention of the corrosion of oil and gas production and transportation equipment; reduction of $H_2S$ concentration in crude oil and natural gas; reduction in viscosity of crude oil; upgradation of heavy crude oils and asphaltenes into lighter hydrocarbon fractions; cleaning of tanks, flowlines and pipelines; enhancing the mobility of oil during water flooding though selective and non-selective plugging; and fracturing fluids. Biosurfactants produced according to the subject invention can also be used for other, non-oil recovery purposes including, for example, cleaning pipes, reactors, and other machinery or surfaces.

In addition to biosurfactants, the subject methods can be useful for producing the powerful emulsifying compound, emulsan. Emulsan is an amphipathic polysaccharide bioemulsifier that interfaces between cell membranes and oil, thus facilitating the process of n-alkanes uptake into the cell. It can also be used to reduce the surface and interfacial tension within an oil well, as well as to make transporting oil through pipelines easier through emulsification of crude oil and lowering viscosity of crude oil. Emulsan is also thought to be useful in other industries, for example, health care, where it might have potential for use as an adjuvant for vaccine delivery.

When used in oil and gas applications, the microbe-based products of the present invention can be used to lower the cost of microbial-based oilfield compositions and can be (though are not required to be) used in combination with other chemical enhancers, such as non-biological polymers, solvents, fracking sand and beads, emulsifiers, surfactants, and other materials known in the art.

Preparation of Microbe-Based Products

The subject invention provides microbe-based products, as well as their use, to improve and/or enhance oil well performance, and/or stimulate oil wells. Preferably, the microbe-based products are formulated based on the potential growth, metabolite production and survivability of the microbes under reservoir conditions.

The microbe-based products of the subject invention are useful for enhanced oil recovery (EOR) and/or well stimulation. Among other mechanisms for improving the performance of an oil well, the microbe-based products are capable of degrading crude oils, reducing surface and interfacial tension of fluids within a well, reducing the viscosity of oil and cleaning contaminants such as paraffins, asphaltenes, and scales, that have obstructed the flow of oil from the well and through equipment.

One microbe-based product of the subject invention is simply the fermentation medium containing the microorganism and/or the microbial metabolites produced by the microorganism and/or any residual nutrients. The product of fermentation may be used directly without extraction or purification. In this sense, the microbe-based product can comprise crude form metabolites, such as biosurfactants and/or biopolymers. In one embodiment, crude form metabolites can take the form of a liquid mixture comprising metabolite sediment in fermentation broth resulting from cultivation of a microbe. This crude form metabolite solution can comprise from about 25% to about 75%, from about 30% to about 70%, from about 35% to about 65%, from about 40% to about 60%, from about 45% to about 55%, or about 50% pure metabolite.

If desired, however, extraction and purification can be easily achieved using standard extraction methods or techniques known to those skilled in the art.

The microorganisms in the microbe-based product may be in an active or inactive form. The microbe-based products may be used without further stabilization, preservation, and storage. Advantageously, direct usage of these microbe-based products preserves a high viability of the microorganisms, reduces the possibility of contamination from foreign agents and undesirable microorganisms, and maintains the activity of the by-products of microbial growth.

The microbes and/or broth resulting from the microbial growth can be removed from the growth vessel and transferred via, for example, piping for immediate use.

In other embodiments, the composition (microbes, broth, or microbes and broth) can be placed in containers of appropriate size, taking into consideration, for example, the intended use, the contemplated method of application, the size of the fermentation tank, and any mode of transportation from microbe growth facility to the location of use. Thus, the containers into which the microbe-based composition is placed may be, for example, from 1 gallon to 1,000 gallons or more. In certain embodiments the containers are 2 gallons, 5 gallons, 25 gallons, or larger.

Upon harvesting the microbe-based composition from the growth vessels, further components can be added as the harvested product is placed into containers and/or piped (or otherwise transported for use). The additives can be, for example, buffers, carriers, other microbe-based compositions produced at the same or different facility, viscosity modifiers, preservatives, nutrients for microbe growth, tracking agents, pesticides, and other ingredients specific for an intended use.

Advantageously, in accordance with the subject invention, the microbe-based product may comprise broth in which the microbes were grown. The product may be, for example, at least, by weight, 1%, 5%, 10%, 25%, 50%, 75%, or 100% broth. The amount of biomass in the product, by weight, may be, for example, anywhere from 0% to 100% inclusive of all percentages therebetween.

Optionally, the product can be stored prior to use. The storage time is preferably short. Thus, the storage time may be less than 60 days, 45 days, 30 days, 20 days, 15 days, 10 days, 7 days, 5 days, 3 days, 2 days, 1 day, or 12 hours. In a preferred embodiment, if live cells are present in the product, the product is stored at a cool temperature such as, for example, less than 20° C., 15° C., 10° C., or 5° C. On the other hand, a biosurfactant composition can typically be stored at ambient temperatures. Even further, if the cells are in spore form, the product is preferably stored and transported at a low temperature, not higher than 15° C., in order to prevent premature germination.

Local Production of Microbe-Based Products

In preferred embodiments of the subject invention, a microbe growth facility produces fresh, high-density microorganisms and/or microbial growth by-products of interest on a desired scale. The microbe growth facility may be located at or near the site of application. The facility produces high-density microbe-based compositions in batch, quasi-continuous, or continuous cultivation.

The distributed microbe growth facilities can be located at the location where the microbe-based product will be used. For example, the microbe growth facility may be less than 300, 250, 200, 150, 100, 75, 50, 25, 15, 10, 5, 3, or 1 mile from the location of use.

The microbe growth facilities of the subject invention produces fresh, microbe-based compositions, comprising the microbes themselves, microbial metabolites, and/or other components of the broth in which the microbes are grown. If desired, the compositions can have a high density of vegetative cells or propagules, or a mixture of vegetative cells and propagules.

Because the microbe-based product is generated locally, without resort to the microorganism stabilization, preservation, storage and transportation processes of conventional microbial production, a much higher density of bacteria cells and/or propagules can be generated, thereby requiring a smaller volume of the microbe-based product for use in the on-site application or which allows much higher density microbial applications where necessary to achieve the desired efficacy. This allows for a scaled-down bioreactor (e.g., smaller fermentation tank, and smaller supplies of starter material, nutrients, pH control agents, and defoaming agents), which makes the system efficient. Local generation of the microbe-based product also facilitates the inclusion of the growth broth in the product. The broth can contain agents produced during the fermentation that are particularly well-suited for local use.

Advantageously, the compositions can be tailored for use at a specified location. The microbe growth facilities provide manufacturing versatility by the ability to tailor the microbe-based products to improve synergies with destination geographies and harness the power of naturally-occurring local microorganisms and their metabolic by-products to improve oil production. Local microbes can be identified based on, for example, salt tolerance and ability to grow at high temperatures.

Advantageously, these microbe growth facilities provide a solution to the current problem of relying on far-flung industrial-sized producers whose product quality suffers due to upstream processing delays, supply chain bottlenecks, improper storage, and other contingencies that inhibit the timely delivery and application of, for example, a viable, high cell-count product and the associated broth and metabolites in which the cells are originally grown.

The microbe-based products of the subject invention are particularly advantageous compared to traditional products wherein cells have been separated from metabolites and nutrients present in the fermentation growth media. Reduced transportation times allow for the production and delivery of fresh batches of microbes and/or their metabolites at the time and volume as required by local demand.

Local production and delivery within, for example, 24 hours of fermentation results in pure, high cell density compositions and substantially lower shipping costs. Given the prospects for rapid advancement in the development of more effective and powerful microbial inoculants, consumers will benefit greatly from this ability to rapidly deliver microbe-based products.

EXAMPLES

A greater understanding of the present invention and of its many advantages may be had from the following examples, given by way of illustration. The following examples are illustrative of some of the methods, applications, embodiments and variants of the present invention. They are not to be considered as limiting the invention. Numerous changes and modifications can be made with respect to the invention.

Example 1—Symbiotic Fermentation of *A. Venetianus* RAG1 and *Bacillus Subtilis* B1

*Acinetobacter venetianus* RAG1 and *Bacillus subtilis* B1 were proven to grow in a synergistic fashion via symbiotic fermentation. Among four carbon sources studied, glucose was shown to be the optimal carbon source for biomass growth and metabolite production for this combination of microorganisms. The cell biomass from symbiotic growth of RAG1 and B1 was greater than pure culture of RAG1. Emulsan and surfactin were produced. Emulsan production of symbiotic culture was greater than pure culture of RAG1. The surface tension of cell supernatant after 10 times dilution dropped from about 62.5 mN/m to about 34 mM/m after 41 h of fermentation.

Methods

Four different carbon sources (glycerol, glucose, isopropyl alcohol and ethanol) were investigated for cultivating RAG1 and B1 in M14 medium. Growth of mixed culture of *A. venetianus* RAG1 and *B. subtilis* B1 were compared with pure culture of *A. venetianus* RAG1 in shaker flasks at 30° C., 200 rpm. Colonies of mixed culture on nutrient broth agar plates after serial dilution were also shown. Surfactin and emulsan production were analyzed by high liquid performance chromatography (HPLC) equipped with a C18 column, using methanol as a mobile phase with acetonitrile gradient from 65% to 80%.

Results

Referring to FIG. 1, the mixed culture systems ("RAG1 B1 glycerol" and "RAG1 B1 glucose") showed the highest growth levels over all the pure culture systems. Although the pure cultures of "RAG1 glucose" and "RAG1 glycerol" showed minimum growth (OD at 600 nm around 0.2), the mixed culture systems showed significantly higher cell concentration (maximum OD600 around 1.2 for glucose and 1.6 for glycerol). Thus, symbiotic growth of *A. venetianus* RAG1 and *B. subtilis* B1 exhibited unexpectedly enhanced biomass production.

Figure 2A:
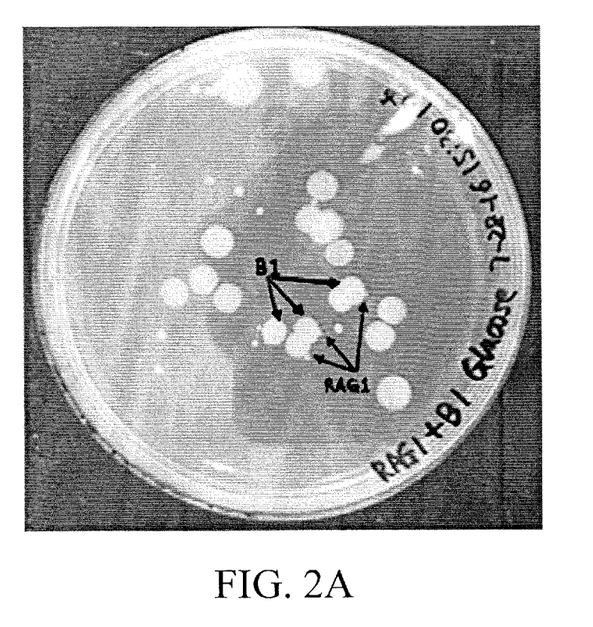
FIGS. 2A-2B represent mixed colonies of *A. venetianus* RAG1 and *B. subtilis* B1 A) on nutrient broth medium with $10^{-6}$ dilution after 29 h of symbiotic fermentation and B) on M14 medium after 14 h of fermentation. Lighter arrows are used to depict *A. venetianus* RAG1, while darker arrows are used to depict *B. subtilis* B1.
Figure 2B:
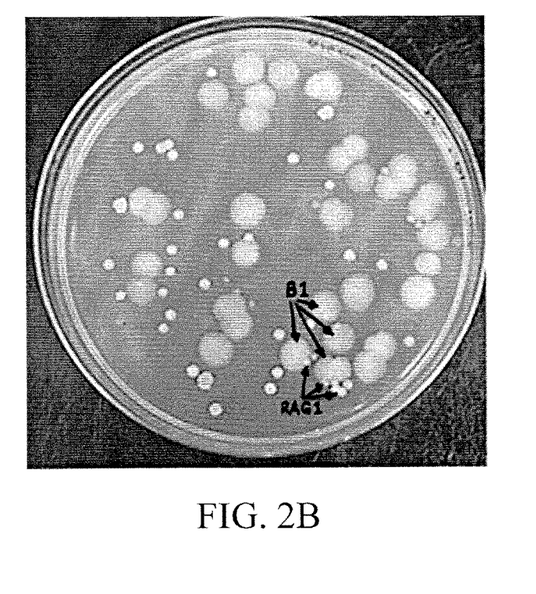

FIG. 2 depicts *A. venetianus* RAG1 and *B. subtilis* B1 growing together. As indicated by the lighter arrows, *A. venetianus* colonies might coalesce with *B. subtilis* B1 colonies. As B1 colonies grow bigger, RAG1 colonies might be buried inside B1 colonies.

After 29 hours of symbiotic fermentation on nutrient broth medium, the RAG1 colony forming unit (CFU) was $3.2 \times 10^8$ CFU/mL, and that of B1 was $3.2 \times 10^8$ CFU/mL, as shown in FIG. 2A.

After 14 hours of symbiotic fermentation on M14 medium, the RAG1 CFU was $8.5 \times 10^8$ CFU/mL and that of B1 was $8.5 \times 10^8$ CFU/ml, as shown in FIG. 2B.

FIG. 3 summarizes metabolite production by *A. venetianus* RAG1 and *B. subtilis* B1. The surface tension of the supernatant of "RAG1 B1 glucose" system after 10× dilution and 41 hours of fermentation dropped to 34.5 mN/m, while those in the other systems remained around 62.5 mN/m. Correspondingly, both emulsan and surfactin production were the highest in "RAG1 B1 glucose" systems.

In conclusion, symbiotic fermentation of *A. venetianus* RAG1 and *B. subtilis* B1 with glucose as a carbon source effectively produced higher biomass and two types of useful metabolites. The surface tension was effectively reduced to 34.5 mN/m even after 10 times dilution of the cell supernatant. The symbiotic growth of bacteria possibly provides the advantages of better utilization of nutrients for biomass and higher value-added metabolic product production.

Example 2—Symbiotic Fermentation of *A. Venetianus* and *Bacillus Subtilis* in a 900 L Distributable Reactor A portable reactor is used comprising two tanks run by a central airlift to help mix the two tanks simultaneously. The reactor has a working volume of 600 L when growing RAG1 and B1 for metabolite production.

In a preferred embodiment, the nutrients for biosurfactant and biopolymer production are glucose, powder molasses, sucrose, potassium phosphate, sodium phosphate, potassium chloride, magnesium sulfate, calcium chloride, urea, ammonium chloride, and yeast extract.

The reactor containing 600 L of nutrient medium with pH 6.8-7.0 is inoculated with 60 liters of seed culture containing both RAG1 and B1. Fermentation continues for 24 hours with no pH stabilization, and a temperature of 28 to 30° C.

The final concentration of cells is up to 1 billion cells/ml of combined culture with approximate equal distribution of both microorganisms.

The invention claimed is:

1. A method of co-cultivating a first microorganism and a second microorganism to produce cellular biomass and/or one or more growth by-products, the method comprising:
    inoculating a fermentation system with the first and second microorganisms;
    providing the fermentation system with a carbon source; and
    incubating the first and second microorganisms under controlled conditions using the fermentation system until a desired amount of cellular biomass and/or a desired amount of the one or more growth by-products has been produced; and
    harvesting the biomass and/or one or more growth by-products from the fermentation system,
    wherein the first microorganism is *Acinetobacter venetianus* RAG1 and the second microorganism is *Bacillus subtilis* B1,
    wherein the growth by-products are emulsan and surfactin, and wherein the amounts of cellular biomass, emulsan and/or surfactin that are produced are greater than the amounts produced when the RAG1 and B1 are cultivated individually.

2. The method of claim 1, wherein the carbon source is selected from the group consisting of glycerol, isopropyl alcohol and ethanol.

3. The method of claim 2, wherein the carbon source is glucose.

* * * * *